(12) United States Patent
Hardie et al.

(10) Patent No.: US 10,216,376 B2
(45) Date of Patent: Feb. 26, 2019

(54) METHOD FOR SPECIFYING A POSITION OF A PATIENT WITH RESPECT TO THE ISOCENTER OF A MEDICAL IMAGING SCANNER

(71) Applicant: Siemens Aktiengesellschaft, Munich (DE)

(72) Inventors: Donald Hardie, Moehrendorf (DE); Anja Jaeger, Fuerth (DE); Stephan Nufer, Erlangen (DE); Thorsten Speckner, Erlangen (DE); Jens Thoene, Nuremberg (DE)

(73) Assignee: Siemens Healthcare GmbH, Erlangen (DE)

(*) Notice: Subject to any disclaimer, the term of this patent is extended or adjusted under 35 U.S.C. 154(b) by 556 days.

(21) Appl. No.: 14/995,428

(22) Filed: Jan. 14, 2016

(65) Prior Publication Data
US 2016/0202864 A1 Jul. 14, 2016

(30) Foreign Application Priority Data
Jan. 14, 2015 (DE) .......... 10 2015 200 474

(51) Int. Cl.
| | |
|---|---|
| *G06F 3/0484* | (2013.01) |
| *G01R 33/30* | (2006.01) |
| *G01R 33/54* | (2006.01) |
| *G06T 7/00* | (2017.01) |
| *G06F 3/0488* | (2013.01) |
| *G01R 33/28* | (2006.01) |

(52) U.S. Cl.
CPC .......... *G06F 3/0484* (2013.01); *G01R 33/307* (2013.01); *G01R 33/546* (2013.01); *G06F 3/04883* (2013.01); *G06T 7/0012* (2013.01); *G01R 33/28* (2013.01); *G06T 2207/10088* (2013.01); *G06T 2207/30196* (2013.01); *G06T 2207/30204* (2013.01)

(58) Field of Classification Search
CPC ........ G01R 33/30; G01R 33/54; G01B 11/24; G06T 7/00; G01G 19/44; H04N 5/225; G06F 3/041; G06F 3/048; G06F 3/0481; G06F 3/0484; G06F 3/0488
See application file for complete search history.

(56) References Cited

U.S. PATENT DOCUMENTS

| | | |
|---|---|---|
| 2004/0081341 A1 | 4/2004 | Cherek et al. |
| 2004/0122311 A1 | 6/2004 | Cosman |
| 2007/0225588 A1 | 9/2007 | Steckner |

(Continued)

FOREIGN PATENT DOCUMENTS

| | | |
|---|---|---|
| CN | 103054579 A | 4/2013 |

*Primary Examiner* — Xiomara L Bautista
(74) *Attorney, Agent, or Firm* — Schiff Hardin LLP (57) ABSTRACT

In a method and medical imaging apparatus for specifying a position of a patient with respect to the isocenter of the scanner of the medical imaging apparatus, position data of the patient are acquired before introducing the patient into the patient-receiving region of the scanner and the acquired position data are evaluated with respect to a patient image. The patient image is transferred to a graphic interface, wherein the patient image is displayed. A position of a patient with respect to the isocenter is specified by determining at least one localization point in the patient image via the graphic interface.

19 Claims, 3 Drawing Sheets

(56) References Cited

U.S. PATENT DOCUMENTS

| | | |
|---|---|---|
| 2010/0156421 A1 | 6/2010 | Sukkau |
| 2011/0082361 A1 | 4/2011 | Jattke et al. |
| 2013/0060129 A1 | 3/2013 | Lee et al. |
| 2014/0037057 A1* | 2/2014 | Kim .................. G01N 23/04 378/62 |
| 2016/0109545 A1 | 4/2016 | Forthmann et al. |
| 2016/0187469 A1* | 6/2016 | Jeong ................ G01S 17/023 356/5.01 |
| 2017/0119339 A1* | 5/2017 | Johnson ................ A61B 6/58 |

* cited by examiner

METHOD FOR SPECIFYING A POSITION OF A PATIENT WITH RESPECT TO THE ISOCENTER OF A MEDICAL IMAGING SCANNER

BACKGROUND OF THE INVENTION

Field of the Invention

The present invention concerns a method for specifying a position of a patient with respect to the isocenter of a medical imaging scanner for a medical imaging examination. The present invention also concerns a medical imaging apparatus that is designed to implement such a method.

Description of the Prior Art

Ideal conditions for a medical imaging examination are found in the isocenter of a medical imaging scanner. For example, the isocenter of a magnetic resonance device is situated in a region in which an optimally homogeneous magnetic field exists. For a magnetic resonance examination the patient, in particular a region of the patient to be examined, should be arranged as precisely as possible in this homogeneity region, or the isocenter.

SUMMARY OF THE INVENTION

An object of the present invention is to enable simple and fast specification of a position of a patient with respect to the isocenter of a medical imaging scanner.

The method in accordance with the invention for specifying a position of a patient with respect to the isocenter of a medical imaging scanner for a medical imaging examination has the following steps. Position data of the patient are acquired before introducing the patient into a patient-receiving region of the medical imaging scanner. The acquired position data are evaluated in a computer with respect to a patient image of the patient. The patient image is transferred to a graphic interface of the computer, where the patient image is displayed. A position of the patient with respect to the isocenter of the scanner is specified by determining at least one localization point in the patient image by the graphic interface.

As used herein "isocenter" means a point and/or a region located inside a patient-receiving region of the scanner in which the most ideal conditions for the medical imaging examination are to be found during operation of the medical imaging scanner. The isocenter preferably describes a point inside an isocenter region. The isocenter inside a magnetic resonance scanner is, for example, a point and/or a region at which the magnetic field of the magnetic resonance scanner is most homogeneous. The isocenter for a medical imaging scanner is preferably specified once during installation of the medical imaging scanner.

Furthermore, as used herein, "position data of the patient" means position data of the patient with respect to a patient-supporting device on which the patient is supported for the pending medical imaging examination. The patient image preferably is an image of the patient supported on the patient-supporting device, so positioning of the patient inside the patient-receiving region, in particular with respect to the isocenter inside the patient-receiving region, can be ascertained using a positioning route (path) of the patient-supporting device. A positioning route and/or a position of the patient-supporting device inside the patient-receiving region of the medical imaging scanner therefore can be adjusted with particular precision by a motor operated by a control computer.

Furthermore, as used herein, a "graphic interface" means a display screen and/or an output presentation unit for display and/or graphic presentation of information to an operator, in particular a medical technician. Moreover, the graphic interface can be designed for the entry of information into the computer by a medical technician. As used herein, a "localization point" means a point on the patient image that specifies a position and/or a region on the patient inside the patient-receiving region of the scanner that at least partially, and preferably completely, coincides with the isocenter.

The inventive method enables simple and fast specification of a position of the patient with respect to the isocenter of a medical imaging scanner. An additional marking unit, such as a laser unit, which marks a localization point on the patient by means of laser light, can advantageously be dispensed, with and a particularly compact medical imaging scanner is thereby provided. Furthermore, complex marking of a localization point by such a marking unit is also omitted in this way, which requires the patient to be moved into the patient-receiving region and to be moved out again. A further advantage of the invention is that the procedure for specifying the position of the patient with respect to the isocenter can take place via the graphic interface, so during this procedure the patient can still be outside the patient-receiving region and the length of time the patient spends inside the patient-receiving region thus can be minimized. This can also contribute to relaxation of the patient.

The graphic interface preferably has a graphic output unit and/or a graphic display scanner, such as a touch display. The display of information and the entry of parameters and/or positioning information can be straightforward for a medical technician in this way. The touch display can be arranged directly on the medical imaging scanner and/or on the patient-supporting device, so for this purpose a medical technician does not need to leave the examination space, in which in the medical imaging scanner is situated.

A touch display means a touch-sensitive screen whereby, by touching sections of the screen, in particular sections of an image displayed on the screen, parameters, such as for controlling a program sequence, can be entered.

Furthermore, specifying the localization point inside the patient image can be implemented by a manual gesture of an operator at the graphic interface. In this way, the position of the patient can be specified with respect to the isocenter particularly quickly by a gesture of the operator. Laborious specification by entries made via an additional input means, such as a keyboard, such as by the use of arrow keys, can be omitted. The manual gesture preferably is the operator stroking and/or swiping and/or dragging at least one finger over the graphic interface. A manual gesture means a gesture that the medical operator performs directly at and/or on the graphic surface, in particular the touch display, and which can be unambiguously allocated to an input command. For example, the manual gesture for specifying the localization point inside the patient image can be moving a graphic positioning element that shows the isocenter and that is displayed on the graphic interface, by the medical operator positioning a finger on a region of the graphic interface that shows the graphic positioning element, and a subsequent movement of the finger in a desired direction on the graphic interface. The localization point is preferably formed by an end point of the graphic positioning element after the conclusion of the manual gesture.

In a further embodiment of the invention, the position data of the patient are acquired by a position data acquisition detector. The position data acquisition detector can be, for example, a camera that acquires two-dimensional or three-dimensional position data. In this way current position data of the patient for specifying the position of the patient with respect to the isocenter of the medical imaging device can be advantageously provided, so a current position of the patient for specifying the position of the patient with respect to the isocenter of the medical imaging device can always be taken into account. The position data acquisition detector is preferably formed independently or separately from the scanner of the medical imaging apparatus. For example, the position data acquisition detector can be camera that is mounted so its field of view "sees" at least a part of the patient receptacle of the scanner.

The position data of the patient preferably map the patient completely, so a particularly straightforward acquisition of the position data of the patient can be achieved, since the patient merely has to be brought into an acquisition region of the position data acquisition unit for this purpose. Complete mapping of the patient means that the position data completely covers or encompasses and/or depicts the patient, in particular a surface and/or a contour of the patient, in the direction of the patient's longitudinal extent. The patient is preferably mapped in a plan view.

In a further embodiment of the invention, during display of the patient image by the graphic interface, a graphic positioning element is also displayed so as to be superimposed on the patient image. The graphic positioning element depicts and/or maps the isocenter of the medical imaging scanner. A position of the patient with respect to the isocenter of the medical imaging scanner can advantageously be specified particularly easily on and/or at the graphic interface by the graphic positioning element, and the workflow for the medical operator is thereby simplified and reduced.

In an embodiment development of the invention the graphic positioning element is a line superimposed on the displayed patient image and/or a point of intersection superimposed on the displayed patient image. The at least one localization point on the patient image, and therewith the isocenter relating to a region of the patient to be examined, thus can be positioned particularly exactly and easily via the graphic interface. The line and/or point of intersection can be designated for example, by crosshairs that are displayed superimposed on the patient image.

In a further embodiment of the invention, at least one accessory examination component for the medical imaging examination is detected using the acquired patient data. The accessory examination component can be positioned particularly exactly with respect to the isocenter of the medical imaging device and/or a position of the patient specified with respect to the isocenter using a position of the accessory examination component. The accessory examination component is advantageously arranged around a region of the patient to be examined, so a position of the patient is also specified with respect to the isocenter by specifying a position of the accessory examination component with respect to the isocenter. The at least one accessory examination component may also be provided with marking elements for reliable detection of the at least one accessory examination component in the acquired position data. Furthermore, the marking elements may be dependent on the type of the accessory examination component, so, moreover, a distinction among a number of accessory examination components and/or a categorization of at least one accessory examination component can be made using acquired position data and/or using acquired marking data.

The accessory examination component can be a local radio-frequency antenna. For example, the accessory examination component for a knee examination can be a local coil or for a head examination, a local head coil. The term "coil" is commonly understood as encompassing one or more RF radiators or RF detectors.

In a further embodiment, using a position of the at least one accessory examination component and/or the type of the at least one accessory examination component, a positioning suggestion is generated and displayed inside the patient image on the graphic interface for positioning of the patient with respect to the isocenter. In this way, a suggestion for positioning of the patient with respect to the isocenter can be automatically presented to the medical operator via the graphic interface using the position and/or type of accessory examination component, for example a local radio-frequency antenna unit, which is used only for examinations of a specific body part. The positioning suggestions can be ascertained using specified position data, such as in the design of the accessory examination component as a head radio-frequency antenna, which always assumes the same position on the patient-supporting device. Furthermore, in the case of accessory examination components such as local radio-frequency antennas that can be freely positioned by a medical operator on the patient-supporting device and/or the patient, a suggestion for positioning of the patient with respect to the isocenter can be ascertained when the type and/or category of local radio-frequency antenna is ascertained using the acquired positioning data. For example, with an identification of a local knee radio-frequency antenna the position suggestion can be a positioning of the knee of the patient and/or local knee radio-frequency antenna inside the isocenter. The positioning suggestion is preferably created automatically and/or independently by an evaluation computer of the medical imaging apparatus.

Particularly simple and fast specification of the position of the patient with respect to the isocenter of the medical imaging scanner can be achieved when the position of the patient with respect to the isocenter is specified for the medical imaging examination by accepting a positioning suggestion. The positioning suggestion is preferably accepted manually by a medical operator. In addition, the positioning suggestion can be checked (verified).

Furthermore, by changing the positioning suggestion, the position of the patient can be specified with respect to the isocenter for the medical imaging examination. Changing the suggestion can be a change in the position of the localization point with respect to the patient image. The positioning suggestion is preferably changed manually by the medical operator by via the graphic interface. Checking and subsequent correction of the positioning suggestion can be implemented. Especially flexible and simple adjustment of the suggested position of the patient with respect to the isocenter can be implemented by the medical operator.

In a further embodiment of the invention, when using a number of accessory examination components, at least one of the multiple accessory examination components is manually selected at the graphic interface, such as by touching a section of a surface of the graphic interface displaying the at least one of the multiple accessory examination components. In this way, a medical operator can easily specify an examination sequence at least partially by choosing the corresponding accessory examination component.

After specifying the position of the patient with respect to isocenter, the patient is introduced into a patient-receiving region of the medical imaging scanner, and the position of the patient inside the patient-receiving region is specified using the at least one localization point. In this way the patient can be brought easily and quickly into a position inside the patient-receiving region that is necessary for the medical imaging examination. The patient can be outside the patient-receiving region of the medical imaging scanner during the determination and/or specification of the desired position, namely of the at least one localization point, so the patient is inside the patient-receiving region only for an optimally short duration.

The invention also encompasses a medical imaging apparatus having a scanner that has a patient-receiving region, wherein the patient-receiving region has an isocenter for a medical imaging examination. The scanner at least partially surrounds the patient-receiving region. The apparatus has an evaluation computer that is in communication with a position data acquisition detector that is designed to acquire a position of a patient supported on a patient-supporting device, and a graphic interface. The evaluation computer, together with the position data acquisition detector and the graphic interface, is designed to implement the method for specifying a position of the patient with respect to the isocenter, as described above.

The inventive apparatus enables simple and fast specification of a position of a patient with respect to the isocenter of the medical imaging scanner. An additional marking unit, such as a laser unit, which marks a localization point on the patient by laser light, can advantageously be dispensed with in this way and a particularly compact medical imaging scanner is thereby provided. In addition, complex marking of a localization point by means of the marking unit can be omitted in this way, which requires the patient to be moved into the patient-receiving region and then moved out again. A further advantage of the invention is that the procedure for specifying the position of the patient with respect to the isocenter can take place via the graphic interface, so during this procedure the patient can still be outside the patient-receiving region and the length of time the patient spends inside the patient-receiving region thus can be minimized. This can also contribute to the relaxation of the patient.

The medical imaging scanner can be of any type known to those skilled in the art. Particularly advantageously, however, the medical imaging scanner is a magnetic resonance scanner and/or a computed tomography scanner and/or a PET (Positron Emission Tomography) scanner.

The advantages of the inventive medical imaging apparatus correspond to the advantages of the inventive method for specifying a position of a patient with respect to the isocenter of the medical imaging scanner for a medical imaging examination, as described above in detail. Features, advantages or alternative embodiments mentioned in this connection are applicable to the other aspects of the invention.

In a further embodiment of the medical imaging apparatus, the position data acquisition detector is a 2D camera or a 3D camera, which is a particularly simple and inexpensive position data acquisition detector.

The position data acquisition detector has a field of view, and the position data acquisition detector is arranged such that the field of view completely encompasses the patient and/or the patient-supporting device. This embodiment of the invention enables simple and fast acquisition of the position data of the patient. The position data acquisition detector is preferably arranged on a housing of the medical imaging scanner and/or in the region of the medical imaging scanner such that the field of view covers a region that is in the direction of insertion of the patient into the patient-receiving region in front of the patient-receiving region. Before the medical imaging examination the patient, supported on the patient-supporting device, is preferably located in this region in front of the patient-receiving region. This allows all preparations for the medical imaging examination to already be concluded on the patient, such as for example applying local radio-frequency antenna units and/or attaching injection units to the patient, etc. For the medical imaging examination, the patient then only has to be moved into the patient-receiving region, and the medical imaging examination started.

The graphic interface preferably functions as a graphic output unit and/or a graphic input unit, such as for example a touch display. Information can be displayed and parameters and/or positioning information input particularly easily in this way. The touch display can be arranged directly on the medical imaging device, so a medical operator does not have to leave an examination space, in which the medical imaging scanner is situated, for this purpose. The graphic interface is preferably arranged on a housing that surrounds the scanner.

DESCRIPTION OF THE PREFERRED EMBODIMENTS

Figure 1:
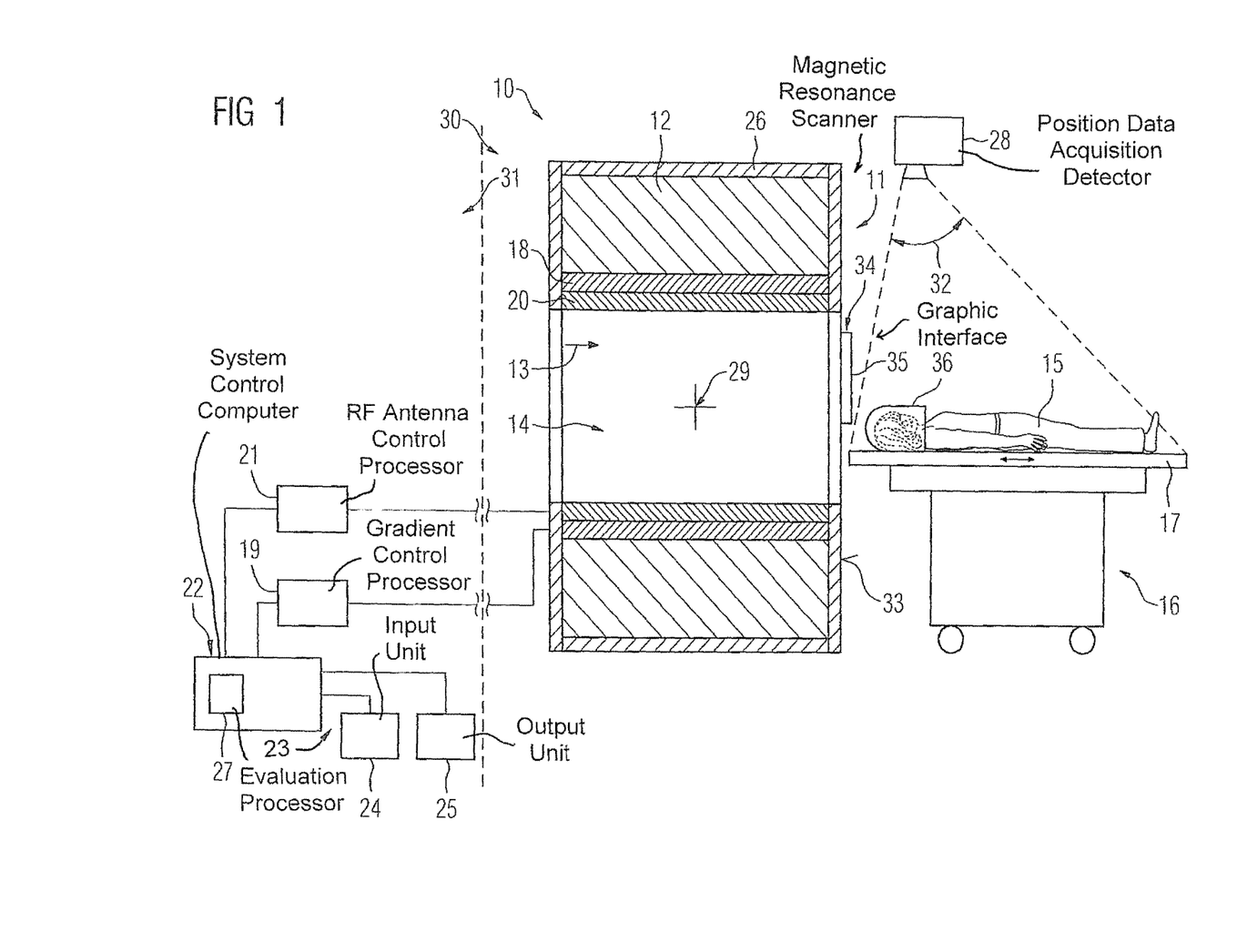
FIG. 1 schematically illustrates a medical imaging apparatus in accordance with the invention.

FIG. 1 schematically shows a medical imaging in accordance with the invention that, in the present exemplary embodiment is formed as a magnetic resonance apparatus 10. The embodiment of the medical imaging apparatus is not limited to a magnetic resonance apparatus 10, but instead the medical imaging apparatus can be formed by any medical imaging device that is considered appropriate to those skilled in the art, such as a computed tomography apparatus, positron emission tomography (PET) apparatus, etc.

The magnetic resonance apparatus 10 comprises a raw data detector formed by a scanner 11. The scanner 11 has a superconducting basic field magnet 12 for generating a strong, constant basic magnetic field 13. The scanner 11 has a patient-receiving region 14 for receiving a patient 15. In the present exemplary embodiment, the patient-receiving region 14 is cylindrical and is cylindrically surrounded in a circumferential direction by the scanner 11. A different design of the patient-receiving region 14 is conceivable. The patient 15 can be moved by a patient support 16 of the magnetic resonance apparatus 10 into the patient-receiving region 14. The patient support device 16 has for this purpose a patient table 17 designed so as to move inside the patient-receiving region 14. Furthermore, the scanner 11 has a housing 26 that surrounds the scanner 11.

The scanner 11 also has a gradient coil assembly 18 that generates magnetic field gradients that are used to spatially encode the MR signals during data acquisition imaging. The gradient coil assembly 18 is controlled by a gradient control processor 19 of the magnetic resonance apparatus 10. The scanner 11 also has a radio-frequency antenna 20 to excite nuclear spins in the patient 15 so as to cause them to deviate from the polarization that is established by the basic magnetic field 13 generated by the basic field magnet 12. The radio-frequency antenna 20 is controlled by a radio-frequency antenna control processor 21 of the magnetic resonance apparatus 10 and radiates radio-frequency magnetic resonance sequences into an examination volume that is substantially formed by the patient-receiving region 14.

Inside the patient-receiving region 14 is an isocenter 29 of the magnetic resonance scanner 11. The isocenter 29 is a point and/or region in which the most ideal conditions for the medical imaging examination are to be found inside the scanner 11, in particular inside the patient-receiving region 14 of the scanner 11. In the exemplary embodiment the isocenter 29 inside the patient-receiving region 14 is a point and/or region at which the basic magnetic field 13 of the magnetic resonance scanner 11 is most homogeneous.

For controlling the basic field magnet 12, the gradient control processor 19 and the radio-frequency antenna control processor 21, the magnetic resonance apparatus 10 has a system control computer 22. The system control computer 22 centrally controls the magnetic resonance apparatus 10, such as to carry out a predetermined imaging gradient echo sequence. In addition, the system control computer 22 has an evaluation processor 27 for evaluating medical image data that are acquired during the magnetic resonance examination.

The system control computer 22 is arranged outside of an examination room 30, in which the scanner 11 is situated. The system control computer 22 is arranged inside a control room or cubicle 31 that is structurally separate from the examination room 30. The system control computer 22 can also communicate with a user interface 23, with an input unit 24 and an output unit 25, arranged inside the control room 31.

The medical imaging apparatus 10 also has a position data acquisition detector 28 designed to detect a position of the patient 15 with respect to the patient support 16, in particular with respect to the patient table 17. The position of the patient 15 with respect to the patient table 17 is detected by the position data acquisition detector 28 immediately before the medical imaging examination. Using the information obtained and/or acquired by the position data acquisition detector 28, the patient 15 can be correctly positioned inside the patient-receiving region 14. The position data acquisition detector 28 can be a camera for acquiring position data of the patient 15. The camera is formed by a 2D camera or 3D camera for acquiring two-dimensional or for acquiring three-dimensional position data. The position data acquisition detector 28 is designed separately from the scanner 11.

Immediately before the magnetic resonance examination the patient support device 16, with the patient 15 located on the patient table 17, is directly in front of the scanner 11, in particular directly in front of the patient-receiving region 14. The position data acquisition detector 28 is arranged with respect to the scanner 11 and/or patient support 16 such that a field of view 32 of the position data acquisition detector 28 completely covers the patient 15 on the patient table 17, together with the patient table 17. In the present exemplary embodiment the position data acquisition detector 28 is mounted on a ceiling and/or wall of the examination room 30 in which the scanner 11 is situated. Alternatively or additionally, the position data acquisition detector 28 may be arranged on the front 33 of the housing 26 of the magnetic resonance scanner 11.

The magnetic resonance apparatus 10 also has a graphic interface 34. The graphic interface 34 is arranged inside the examination room 30. In the present exemplary embodiment the graphic interface 34 is directly integrated on the housing 26 of the scanner 11. The graphic interface 34 is arranged directly on the front 33 of the housing 26. The arrangement of the graphic interface 34 on the housing 26, in particular on the front 33 of the housing 26, can be accomplished by an integration of the graphic interface 34 into the housing 26. The front of the housing 26, in particular a front housing shell of the housing 26, can have a recess for integration of the graphic interface 34. Alternatively, the graphic interface 34 may be arranged on the housing 26, in particular a front housing shell of the housing 26.

The graphic interface 34 has a touch display 35, so information and/or data can be entered and shown directly via the graphic interface 34.

Figure 2:
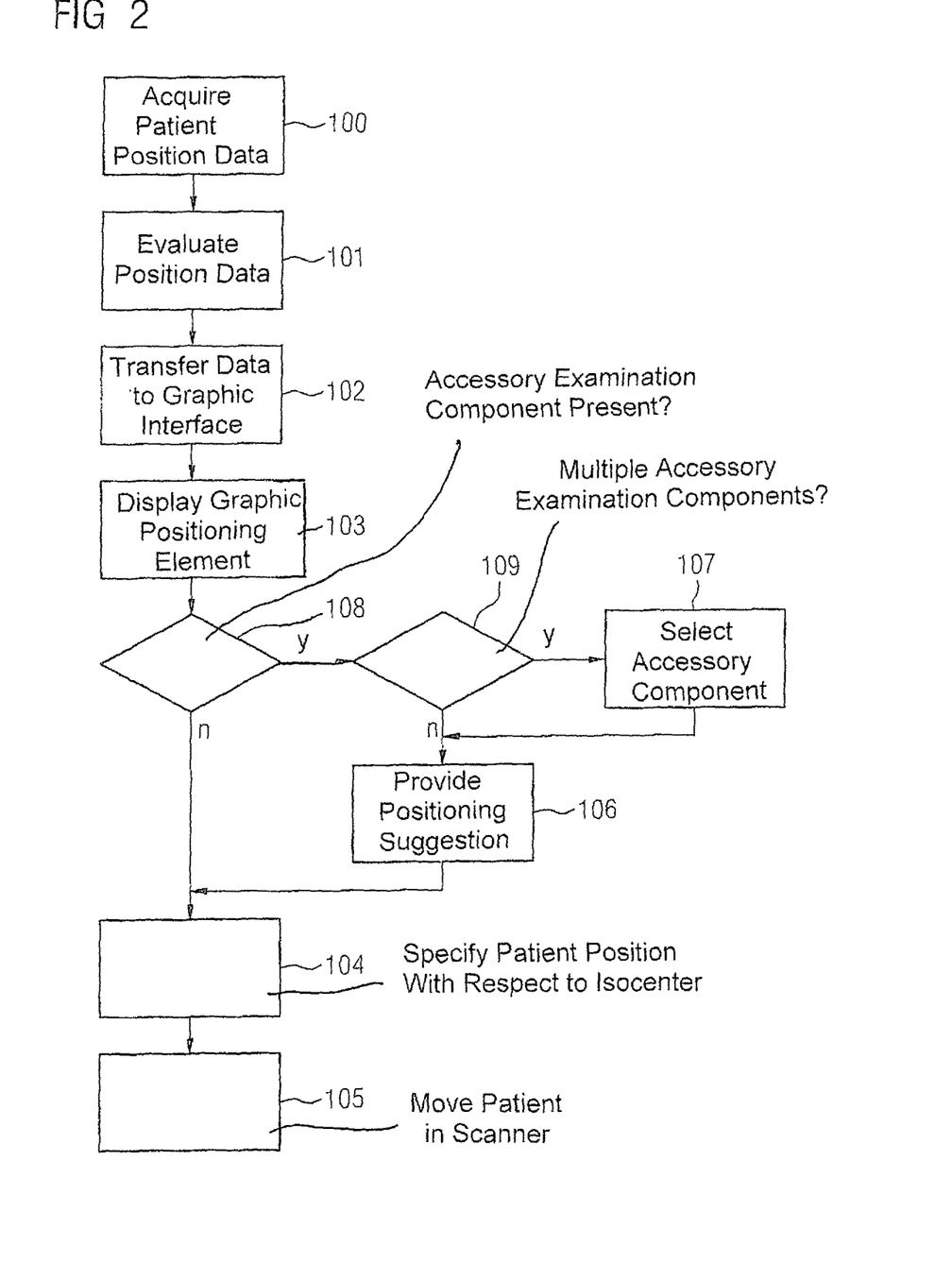
FIG. 2 shows an inventive method for specifying a position of a patient with respect to the isocenter of a medical imaging apparatus for a medical imaging examination.

The evaluation processor 27 together with the position data acquisition detector 28 and graphic interface 34, in particular the touch display 35, are designed to carry out a method for specifying a position of the patient 15 with respect to the isocenter 29 of the medical imaging scanner 11 of the magnetic resonance apparatus 10. FIG. 2 shows a sequence of the method for specifying a position of the patient 15 with respect to the isocenter 29 of the medical imaging scanner 11 in more detail. For this purpose the evaluation processor 27 is connected to the position data acquisition detector 28 and the touch display 35 by a data transfer arrangement (not shown). Data transfer can be wired or wireless between the individual components.

The evaluation processor 27 has for this purpose software and/or computer programs that can be loaded directly into a memory (not shown) of the programmable system control computer 22. The software and/or computer programs have program code to carry out the method for specifying the position of the patient 15 with respect to the isocenter 29 of the medical imaging scanner 11.

At the beginning of the method for specifying the position of the patient 15 with respect to the isocenter 29 of the scanner 11, the patient 15 is already supported on the patient support 16, namely the patient table 17 of the patient support 16. Furthermore, all preparations for the pending medical imaging examination, in particular magnetic resonance examination, have already been concluded on the patient 15. All accessory examination components 36, such as local radio-frequency antenna units, required for the pending medical imaging examination, in particular the magnetic resonance examination, have already been positioned on the patient 15. Furthermore, at the beginning of the method the patient support 16, in particular the patient table 17 of the patient support 16, is also already in a position with respect to the patient-receiving region 14, which already enables movement of the patient 15 into the patient-receiving region 14.

At the beginning of the method, position data of the patient 15 are acquired in a first method step 100 by the position data acquisition detector 28. Depending on the embodiment of the position data acquisition detector 28 as a 2D camera or 3D camera, two-dimensional position data or three-dimensional position data of the patient 15 and the patient's position with respect to the patient support 16, in particular of the patient table 17 of the patient support 16, are therefore acquired. If accessory examination components 36, such as local radio-frequency antenna units, are applied to and/or arranged on the patient 15, then position data of the local radio-frequency antenna units applied to and/or arranged on the patient 15 are also acquired by the acquisition of the position data of the patient 15. The patient data acquired by means of the position data acquisition detector 28 completely cover (encompass) the patient 15 as well as the accessory examination components 36, such as local radio-frequency antenna units, applied to and/or arranged on the patient 15. The patient 15, together with the patient table 17 and optionally further accessory examination components 36, is acquired in a plan view from above. In addition, an only partial acquisition of the patient 15, in particular of sections of the patient 15, and/or of accessory examination components 36 is also conceivable, with a section relevant to the pending medical imaging examination being acquired and/or mapped by the position data.

The acquired position data are then evaluated in a further method step 101. The evaluation occurs in the evaluation processor 27. For this purpose, first the position data are transferred from the position data acquisition detector 28 to the evaluation processor 27 via the data transfer arrangement. The evaluation processor 27 ascertains a patient image, in which the patient 15 is shown in the patient's position on the patient table 17. If accessory examination components 36, such as local radio-frequency antenna units, are applied to and/or arranged on the patient 15, the position data of the local radio-frequency antenna units applied to and/or arranged on the patient 15 are also evaluated in method step 101 of evaluation of the acquired position data of the patient 15, and shown on the reconstructed and/or ascertained patient image.

If the patient 15 has been completely acquired by the position data acquisition detector 28 in the first method step 100, the ascertained patient image also completely maps the patient 15 and/or accessory examination components 36 arranged on and/or applied to the patient 15, so the patient 15 is shown so as to be completely seen, together with the accessory examination components 36 arranged on and/or applied to the patient 15, in the ascertained patient image.

Figure 3:
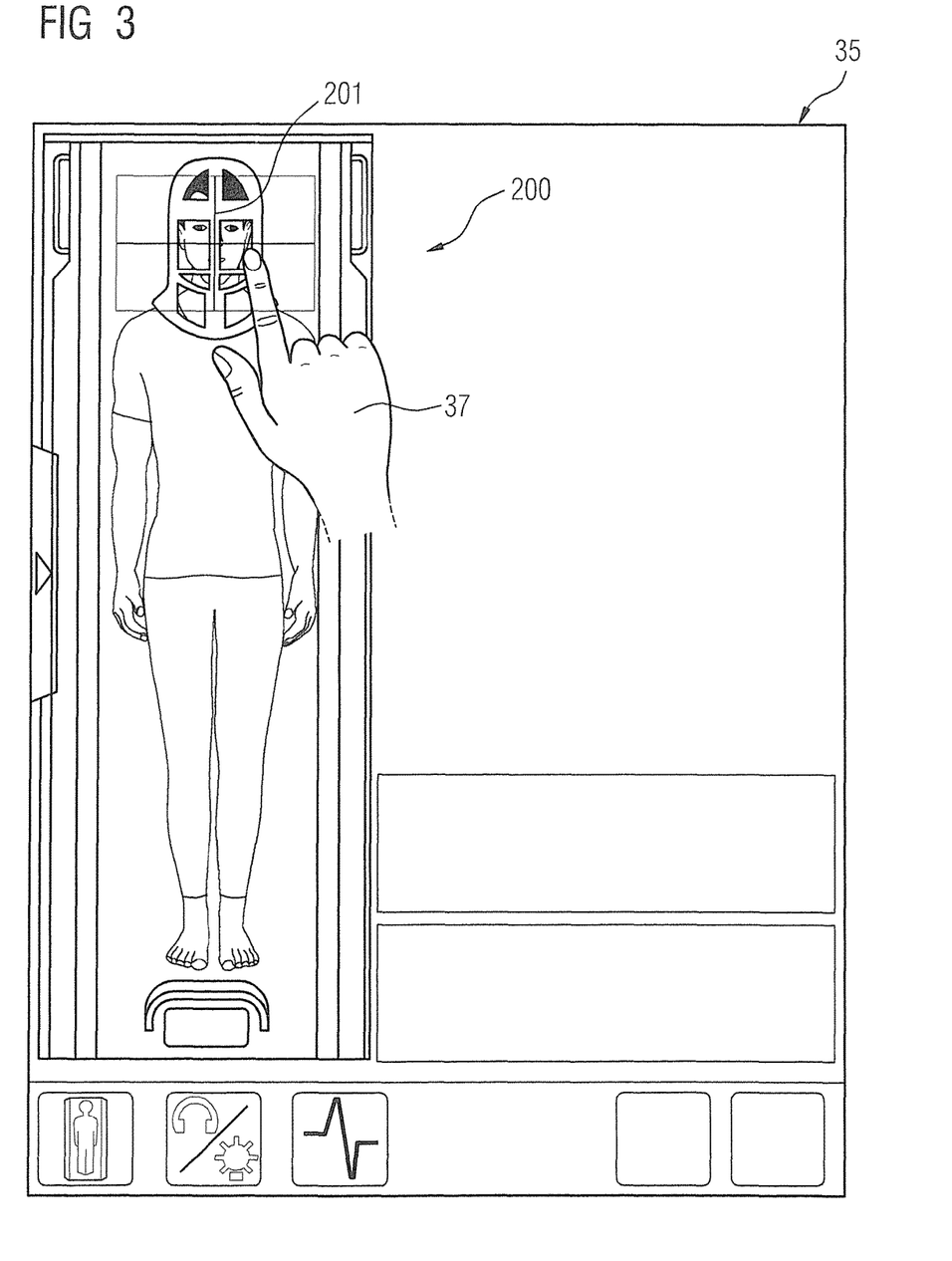
FIG. 3 shows an exemplary embodiment of a graphic interface presentation.

In a subsequent method step 102, the evaluated and/or ascertained patient image is transferred by the data transfer arrangement to the graphic interface 34, in particular to the touch display 35 of the graphic interface 34. FIG. 3 shows an exemplary, schematically depicted screenshot that includes a patient image 200 on the touch display 35 with an accessory examination component 36 designed as a head radio-frequency antenna. Via the touch display 35, the ascertained and/or evaluated patient image is graphically depicted in a further method step 103. In this further method step 103 a graphic positioning element 201 is likewise displayed at the graphic interface 34, in particular the touch display 35. The graphic positioning element 201 is shown superimposed on the patient image 200. The graphic positioning element 201 identifies the isocenter 29 of the scanner 11. In the exemplary embodiment the graphic positioning element 201 is formed by a cross, in particular by crosshairs. A different design of the graphic positioning element 201 is also conceivable, such as a line and/or a single point of intersection and/or an arrow, etc.

A first query 108 then follows as to whether one or more accessory examination component(s) 36 were ascertained and/or determined in the acquired position data. If no accessory examination component 36 was ascertained and/or determined in the acquired position data by the evaluation processor 27 in method step 101, the result of the query 108 is "no" and in a further method step 104 the position of a patient 15 is specified with respect to the isocenter 29, so for a subsequent medical imaging examination an examination region of the patient 15 coincides as much as possible with the isocenter 29 of the scanner 11. For this purpose, at least one localization point is determined via the graphic interface 34, in particular the touch display 35 thereof, in the patient image 200. The localization point identifies the position of the isocenter 29 with respect to the patient 15. In an examination position of the patient 15 inside the patient-receiving region 14, the determined localization point should coincide with the isocenter 29.

The localization point inside the patient image 200 is at least partly determined manually by the medical operator by moving the graphic positioning element 201 on the patient image 200 displayed on the touch display 35. The graphic positioning element 201 is moved by a manual gesture, in particular a sliding gesture and/or swiping gesture, by a finger 37 of the medical operator on the touch display 35. A start point of the manual gesture is preferably formed by a start position of the graphic positioning element 201 and an end point of the manual gesture by a desired end position of the graphic positioning element 201. Once the desired end position of the graphic positioning element 201 has been reached, this can be specified, for example, by a confirmation gesture, such as touching a confirmation area of the touch display 35. At least one localization point is set on the patient image 200 via the touch display 35 for the desired end position of the graphic positioning element 201. The localization point marks the point and/or region of the patient 15 on the patient image 200 that should be situated in the isocenter 29 for the medical imaging examination.

After the method step 104 of specifying the position of a patient 15 with respect to the isocenter 29, the patient 15 is introduced in a further method step 105 inside the patient-receiving region 14 of the medical imaging device by operation of the movably mounted patient table 17.

The position of the patient 15 inside the patient-receiving region 14 is determined and/or specified using the at least one localization point of the patient 15, which should coincide with the isocenter 29 of the scanner 11. The patient 15 is introduced by operation of the patient table 17, controlled by the evaluation processor 27, with a position of the patient table 17 being determined using a positioning route of the patient table 17.

If an accessory examination component 36 was ascertained and/or determined in the acquired position data by the evaluation processor 27 in method step 101, the result of the query 108 is "yes" and as an alternative to the at least partly manual specification of the position of a patient 15 with respect to the isocenter 29 via the touch displays 35 an at least partly automatic and/or independent specification of the position of the patient 15 with respect to the isocenter 29 occurs by operation of the evaluation processor 27. If, for example, accessory examination components 36, such as local radio-frequency antenna units, are applied to and/or arranged on the patient 15, these accessory examination components 36 can be detected immediately by the evaluation processor 27 as accessory examination components 36 using the acquired position data in further method step 101 of evaluating the position data of the patient 15.

For error-free detection, the accessory examination components 36 may also be provided with marking elements, so there can be a clear allocation and/or identification and/or position detection of the accessory examination components 36 by the evaluation processor 27. Different markings for example can be used respectively for different local radio-frequency antenna units.

If the result of the query 108 is "yes", a further query 109 is made as to whether multiple accessory examination components 36 were ascertained and/or determined in the acquired position data. In the case of just one accessory examination component 36 ascertained and/or determined in the acquired position data the result of the query 109 is "no" and a positioning suggestion is ascertained by the evaluation processor 27 in a further method step 106. If, for example, only a single local radio-frequency antenna unit is used for the medical magnetic resonance examination, then this is normally arranged on the section to be examined and/or around the section of the patient 15 to be examined for the pending magnetic resonance examination. A positioning suggestion is therefore automatically and/or independently generated in the further method step 106 by the evaluation processor 27 using a position and/or using the type of local radio-frequency antenna unit. The positioning suggestion is a suggestion relating to the positioning of the patient 15 with respect to the isocenter 29. The positioning suggestion can be ascertained by the evaluation processor 27 such as by using the type of a used local radio-frequency antenna unit. When using local radio-frequency antenna units with a specifically defined position on the patient table 17, the positioning suggestion for the position of the patient 15 with respect to the isocenter 29 is therefore also specified using this specifically defined position of the local radio-frequency antenna unit. When using freely positionable local radio-frequency antenna units, the size of the local radio-frequency antenna unit can be determined for example using a determination of the type, and the positioning suggestion designates the center of the local radio-frequency antenna unit. This positioning suggestion is then displayed, together with the patient image 200, for the medical operator by means of the touch display 35.

After method step 106, the medical operator can specify the localization point inside the patient image 200, and therewith also the position of the patient 15 with respect to the isocenter 29, in method step 104 wherein the position of a patient 15 with respect to the isocenter 29 is finalized by manual acceptance of the positioning suggestion provided by the evaluation processor 27. There is also the possibility that in method step 104 of finalizing the position of a patient 15 with respect to the isocenter 29 by modifying the positioning suggestion generated by the evaluation processor 27 by a manually made change and/or adjustment by the medical operator. Changing and/or adjusting the suggestion means a change to the localization point inside the patient image 200 and thus also a change in the position of the patient 15 with respect to the isocenter 27.

If multiple accessory examination components 36 were ascertained and/or determined in the acquired position data, the result of the query 109 is "yes" and a single accessory examination component 36 is then first chosen among the multiple accessory examination components 36 via the touch display 35 in a further method step 107. The choice of a single accessory examination component 36 among the multiple accessory examination components 36 is made manually in further method step 107 by the medical operator making a choice by touching one of a number of sections of the surface of the touch display 35 that respectively show one of the multiple accessory examination components 36 respectively. This touching of the chosen region of the surface of the touch display 35 is designed by the graphic interface 34 together with the evaluation processor 27 as an acknowledgement command for selection of the chosen accessory examination component 36. The accessory examination components 36 can each be formed, for example, by a local radio-frequency antenna unit, such as for example a head radio-frequency antenna unit and/or a chest radio-frequency antenna unit, etc.

As an alternative to the manual choice of one of the accessory examination components 36, one accessory examination component 36 is chosen at least partly automatically by the evaluation processor 27 in further method step 107. For example, the evaluation processor 27 can present the medical operator with a suggestion of the choice via the touch display 35.

Method step 106 of automatic and/or independent creation of a positioning suggestion by the evaluation processor 27 follows method step 107 of the choice of the one accessory examination component 36. A positioning suggestion is generated in the further method step 106 using the position and/or the type of the chosen local radio-frequency antenna unit. The positioning suggestion is a suggestion relating to the positioning of the patient 15 with respect to the isocenter 29. This positioning suggestion is then displayed for the medical operator via the touch display 35.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for identifying a position of a patient with respect to an isocenter of a medical imaging apparatus, comprising:
    before moving a patient into a medical data acquisition scanner, having an isocenter, in order to acquire medical image data from the patient by operation of the scanner, acquiring position data of the patient while the patient on a patient support is outside of the scanner;
    providing the acquired position data to a computer and correlating said position data with a patient image of the patient;
    transferring the patient image to a graphic interface and displaying the patient image at the graphic interface; and
    designating a localization point in the patient image displayed at the graphic interface, and also displaying a graphic positioning element superimposed on the patient image, said graphic positioning element designating said isocenter with respect to said patient image, and designating said localization point by manipulating said graphic positioning element with respect to the patient image via the graphic interface; and
    from the designation of the localization point on the displayed patient image and using the correlation of the position data with the patient image, automatically specifying, in said computer, a position of the patient outside of the scanner relative to said isocenter and formulating an electrical signal in said computer to cause the patient support to move with the patient thereon into the scanner to make said localization point to coincide with the isocenter, and making the electrical signal available from the computer in a form for operating the patient support.

2. A method as claimed in claim 1 comprising displaying the patient image on a touchscreen of said graphic interface, and designating said localization point by manual interaction with said touchscreen.

3. A method as claimed in claim 2 comprising designating said localization point by a manual gesture with respect to said touchscreen.

4. A method as claimed in claim 1 comprising acquiring the position data of the patient with a position data acquisition detector.

5. A method as claimed in claim 1 comprising acquiring said position data of the patient that completely map the patient.

6. A method as claimed in claim 1 comprising selecting said graphic positioning element from the group consisting of a line and a point.

7. A method as claimed in claim 1 comprising, when acquiring said patient data, also acquiring accessory data representing at least one accessory component to be used when acquiring said medical image data from the patient with said scanner.

8. A method as claimed in claim 7 wherein said scanner is a magnetic resonance data acquisition scanner, and comprising employing a local radio-frequency antenna as said accessory.

9. A method as claimed in claim 7 comprising, when acquiring said position data of the patient, acquiring said accessory data as data selected from the group consisting of data designating a position of said accessory and data designating a type of said accessory, and using said accessory data in said computer to generate a positioning suggestion with respect to the patient for said accessory, and presenting said positioning suggestion at said graphic interface by automatically superimposing a graphic representation of said accessory on said patient image displayed at said graphic interface dependent on said positioning suggestion.

10. A method as claimed in claim 9 comprising accepting said positioning suggestion by a manual acceptance entry made via said graphic interface.

11. A method as claimed in claim 9 comprising allowing an operator to manually move said graphic representation of said accessory superimposed on the patient image at said graphic interface in order to change said positioning suggestion.

12. A method as claimed in claim 7 wherein said accessory is one of a plurality of accessories, and displaying respective designations of said plurality of accessories at respective, different areas on said graphic display, and allowing a manual selection of one of said accessories by manual interaction with a respective one of the areas on said graphic display.

13. A method as claimed in claim 1 comprising controlling operation of said patient support with said computer to move said patient support into a patient-receiving region of said scanner to cause said localization point to coincide with said isocenter.

14. A medical imaging apparatus comprising:
a medical data acquisition scanner having an isocenter;
a patient support adapted to receive a patient thereon from whom medical data are to be acquired by operation of the scanner;
a position data acquisition detector configured to acquire position data of the patient while the patient is outside of the scanner on the patient support, before moving the patient into a medical data acquisition scanner in order to acquire medical image data from the patient by operation of the scanner;
a computer provided with the acquired position data, said computer being configured to correlate said position data with a patient image of the patient;
said computer being configured to transfer the patient image to said graphic interface and said graphic interface being configured to display the patient image at the graphic interface; and
said graphic interface being configured to designate a localization point in the patient image displayed at the graphic interface, and also to display a graphic positioning element superimposed on the patient image, said graphic positioning element designating said isocenter with respect to said patient image, and to designate said localization point by manipulating said graphic positioning element with respect to the patient image via the graphic interface; and
from the designation of the localization point on the displayed patient image and using the correlation of the position data with the patient image, said computer being configured to automatically specify a position of the patient outside of the scanner relative to said isocenter and to formulate an electrical signal and to move the patient support with the patient thereon into the scanner to cause said localization point to coincide with the isocenter, and to provide the electrical signal from the computer to operate the patient support.

15. A medical imaging apparatus as claimed in claim 14 wherein said position data acquisition detector is a camera selected from the group consisting of 2D cameras and 3D cameras.

16. A medical imaging apparatus as claimed in claim 15 wherein said position data acquisition detector has a field of view, and wherein said position data acquisition detector is situated so that said field of view completely encompasses the patient and the position data of the patient completely map the patient.

17. A medical imaging apparatus as claimed in claim 14 wherein said graphic interface comprises a touchscreen at which said patient image is displayed.

18. A medical imaging apparatus as claimed in claim 14 wherein said scanner comprises a scanner housing, and wherein said graphic interface is mounted on said housing.

19. A non-transitory, computer-readable data storage medium encoded with programming instructions, said storage medium being loaded into a control computer of a medical imaging apparatus that comprises a medical data acquisition scanner and a position data acquisition detector, said programming instructions causing said control computer to:
before moving a patient into a medical data acquisition scanner, having an isocenter, in order to acquire medical image data from the patient by operation of the scanner, receive position data of the patient while the patient is outside of the scanner;
correlate said position data with a patient image of the patient;
transfer the patient image to a graphic interface and display the patient image at the graphic interface;
receive a designation of a localization point in the patient image displayed at the graphic interface, and also display a graphic positioning element superimposed on the patient image, said graphic positioning element designating said isocenter with respect to said patient image, and designate said localization point by manipulating said graphic positioning element with respect to the patient image via the graphic interface; and
from the designation of the localization point on the displayed patient image and using the correlation of the position data with the patient image, automatically specify a position of the patient outside of the scanner relative to said isocenter and formulate an electrical signal to cause the patient support with the patient thereon to be moved into the scanner to make said localization point to coincide with the isocenter, and make the electrical signal available from the computer in a form for operating the patient support.

* * * * *